United States Patent [19]

Elton

[11] Patent Number: 5,179,174
[45] Date of Patent: Jan. 12, 1993

[54] FLEXIBLE LUBRICIOUS ORGANIC COATINGS

[75] Inventor: Richard K. Elton, Glens Falls, N.Y.

[73] Assignee: C. R. Bard, Inc., Murray Hill, N.J.

[21] Appl. No.: 751,975

[22] Filed: Aug. 30, 1991

Related U.S. Application Data

[62] Division of Ser. No. 512,872, Apr. 23, 1990, Pat. No. 5,077,352.

[51] Int. Cl.⁵ .................... C08L 71/02; C08L 75/04
[52] U.S. Cl. ........................ 525/409; 525/937; 528/904; 428/423.1
[58] Field of Search ............... 525/409, 937; 528/904

[56] References Cited

U.S. PATENT DOCUMENTS 4,487,808  12/1984  Lambert ........................ 428/423.1
4,990,357  2/1991  Karakelle et al. ............... 525/125

Primary Examiner—Carman J. Seccuro, Jr.
Assistant Examiner—Thomas Hamilton, III
Attorney, Agent, or Firm—Morgan & Finnegan

[57] ABSTRACT

A flexible, lubricious organic polymeric coating is formed by applying a mixture of an isocyanate, a polyol, poly(ethylene oxide), and carrier liquid to a surface to be coated. The carrier liquid is removed and the mixture reacted to form a polyurethane coating with associated poly(ethylene oxide) giving a highly lubricious, abrasion resistant, flexible coating particularly suitable for use as a protective lubricious coating on devices introduced into the body.

5 Claims, 1 Drawing Sheet

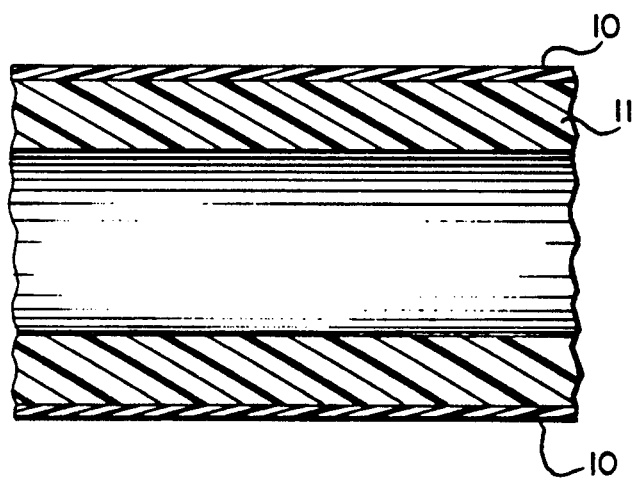

FLEXIBLE LUBRICIOUS ORGANIC COATINGS

This application is a division of application Ser. No. 07/512,872 filed on Apr. 23, 1990, U.S. Pat. No. 5,077,352.

BACKGROUND OF THE INVENTION

It has long been known that hydrophilic coatings with low friction (coeficient of friction of 0.3 or less) are useful for a variety of medical devices such as catheters, catheter introducers and the like. When low friction surfaces are used, such devices when introduced into the body slide easily within arteries, veins, cannula and other body orifices and passageways. There have been a wide variety of methods used to provide the surfaces desired. In some cases the material of the catheter or medical device is formed of a material having good anti-friction properties such as teflon or other plastics which tend to avoid abrasion with the body. However, in many cases a selection of materials does not provide the anti-slip properties desired in conjunction with other desirable properties for the particular medical device.

The art has recognized that polymer surfaces can be provided with hydrophilic coatings formed from combinations of isocyanate, polyurethane and polyvinyl pyrrolidone. Others have suggested applying solutions of poly(ethylene oxide) with isocyanate and/or polyurethane in multi-step operations. Often coatings thus formed can lack good adherence to a substrate in combination with high-slip properties. For example, U.S. Pat. Nos. 4,459,317 and 4,487,808 to Lambert disclosed medical devices having hydrophilic coatings formed from an isocyanate layer overcoated with a poly(ethylene oxide) layer. However, such coatings appear to be of polyurea materials formed from a first solution of an isocyanate being applied to a base with a solvent evaporated, followed by a second solution application of poly(ethylene oxide) in turn followed by evaporation of the solvent. Cure is effected by baking in the presence of moisture, thus producing a polyurea. This type of application appears to provide polyurea materials which do not have the tenacity of the coatings of the present inventions. The multistep procedure makes it difficult to tailor properties and values of the final coatings. The coatings of the present invention are the result of polyurethane linkages in combination with an association of poly(ethylene oxide). The use of a one-dip process and formation of polyurethane has been found particularly useful to provide low-friction coatings which are abrasion resistant in the body, hydrophilic and lubricious.

BRIEF DESCRIPTION OF THE DRAWINGS

The FIGURE is an axial cross sectional view through a portion of a catheter body carrying an abrasion resistant, flexible hydrophilic, lubricious organic coating in accordance with this invention.

SUMMARY OF THE INVENTION

It is the object of this invention to provide an abrasion resistant, hydrophilic, lubricious organic coating which has good adherence to substrates.

It is another object of this invention to provide coatings in accordance with the preceding object which are particularly useful for application to outer surfaces of inorganic materials or organic polymeric medical devices with good adherence to the devices and which are non toxic and non-deleterious to the body.

Another object of this invention is to provide a method of applying an abrasion resistant, hydrophilic, lubricious organic coating as in the preceding objects, which method can be carried out using a single coating solution and using substantially conventional methods in efficient production with good reliability and predictability.

A still further object of this invention is to provide a method in accordance with the preceding objects which provides a flexible urethane coating having a poly(ethylene oxide) associated therewith and which is highly adherent to underlying substrates of varying organic polymeric materials.

According to the invention an abrasion resistant, hydrophilic, lubricious, organic coating is formed from the reaction on a surface to be coated, of a mixture containing an isocyanate, a polyol and a poly(ethylene oxide) in a carrier liquid to form a urethane coating having good adherence to the substrate and good anti-friction properties. The coating can be formed on various medical devices including catheters and catheter introducers.

Accordingly to the method of this invention, a coating as defined above is formed by applying a solution of the mixture and carrier liquid to the substrate by conventional coating methods, including spraying, dipping, painting and the like followed by drying to remove the carrier liquid. In a subsequent step, the coating formed is cured to form a polyurethane having associated poly(ethylene oxide).

It is a feature of this invention that the coating will imbibe water and become lubricious upon exposure to water or aqueous fluids as within the body. The coating can be wetted before introduction into the body Because it is a cross-linked system resulting from a curing operation, the coating will remain firmly bonded to a substrate even when hydrated. The coating resists abrasion having superior durability when compared with many other hydrophilic coatings. The coating can be dried and remoistened repeatedly while retaining its lubricating properties. While the exact mechanism is not definitely known, it appears that the polyol and isocyanate react to form a cross-linked urethane matrix which forms an association complex with the poly(ethylene oxide). In addition, any terminal hydroxyl groups present in the poly(ethylene oxide) chains react with the isocyanates to covalently bond to the polyurethane network. Thus the poly(ethylene oxide) becomes an integral part of the polyurethane coating.

DESCRIPTION OF PREFERRED EMBODIMENTS

An abrasion resistant coating 10 of this invention is shown in the figure overlying a catheter body 11 formed of a flexible organic polymeric material.

The coating 10 is formed from a mixture containing an isocyanate, a polyol and poly(ethylene oxide) in a carrier liquid.

In addition, the mixture can contain additives to alter the characteristics of the coatings in substantially known manners. For example, conventional additives include antioxidants, catalysts, flow control agents, surfactants and air release agents.

Preferably the ratio of weight of isocyanate and polyol to poly(ethylene oxide) varies from 0.25 to 6.0 and preferably 0.75 to 2.0. The stochiometric ratio of total NCO groups in the isocyanate to total OH groups in the polyol can vary from 0.6 to 3.5 and preferably 0.85 to 1.5.

Generally, the coating mixture is preferably a solution. The coating mixture in solution form is prepared by weighing the appropriate quantities of isocyanate, polyol and poly(ethylene oxide) stock solution and adding them into an appropriate mix vessel. Additional solvents can be added to adjust the viscosity. Solids contents in a range of from 0.4 to 40% are preferred. This solution is mixed well and then applied to an appropriate organic substrate which can include catheter tubes, introducers, body implants, medical wires, stents and dilation balloons by conventional coating applying methods. Such methods include dipping, spraying, wiping, painting and the like.

After applying the coating solution, the solvent is preferably allowed to evaporate from the coated substrate often by exposure to ambient conditions for from 10 to 180 minutes but can be evaporated at temperatures of from 35° F. to 400° F. for time periods of a few seconds to overnight, depending upon the selection of solvent and the speed with which evaporation is desired. The coating is then cured. The cure time and temperatures vary with the choice of isocyanate and polyol and the composition of the substrate. This choice of ingredients also affects the physical properties of the overall coating.

Cure temperatures may range from 75° F. to 350° F. Cure times may vary from 2 minutes to 72 hours, depending upon the reactivity of the isocyanate and polyol, and the cure temperature. In all cases the cure conditions are to be non-deliterious to the underlying substrate.

After the coating 10 is formed, the coating can imbibe water from an aqueous solution prior to introduction to the body and can become lubricious. The coating can imbibe water solely from body fluids, even if not introduced to water prior to introduction into the body. Because the coating is a cross-linked system, it adheres well to the substrate even when hydrated. The coating is found to resist abrasion, and exhibits superior durability. It can be dried and remoistened repeatedly and it will retain its lubricating properties. In all cases, the materials are selected so as to be compatible with the body and non-toxic to the body, if the coating is to be used in a body related application as in catheters, introducer tubes and the like.

The organic substrates that can be coated with the coatings of this invention include polyether block amide, polyethylene terephthalate, polyetherurethane, polyesterurethane, natural rubber, rubber latex, synthetic rubbers, polyester-polyether copolymers, ethylene methacrylic acid di-and inter polymers containing metal salts, polyethers, polyesters, and other polyurethanes, polycarbonates, polytetramethylene glycol ether urethane, and other organic materials including poly vinyl chloride and other vinyl polymers, polyethylene and the like, as well as blends and alloys of the above. Other substrates include metals such as stainless steel of guide wires and other devices. Some of these materials are available under the trademarks such as Pebax available from Atochem, Inc. of Glen Rock, N.J., Mylar available from E. I. duPont deNemours and Co. of Wilmington, Del., Texin 985A from Mobay Corporation of Pittsburgh, Pa., Surlyn available from E. I. duPont deNemours and Co. of Wilmington, Del., Pellethane available from Dow Chemical of Midland, Mich., and Lexan available from General Electric Company of Pittsfield, Mass.

The poly(ethylene oxide) preferrably has a mean molecular weight of from about 50,000 to 5,000,000. The isocyanate used are preferably isocyanates having at least two unreacted isocyanate groups per molecule and include but are not limited to polymethylenepolyphenyl isocyanate, 4,4'-diphenylmethane diisocyanate and position isomers thereof, 2,4-tolylene diisocyanate and position isomers thereof, 3,4-dichlorophenyl diisocyanate and isophorone isocyanate, Adducts or prepolymers of isocynates and polyols such as the adduct of trimethylolpropane and diphenylmethane diisocyanate or tolylene diisocyanate are suitable. For further examples of polyisocyantes useful in this invention see Encyclopedia of Polymer Science and Techonology, H. F. Mark, N. G. Gaylord and N. M. Bikales (eds.), (1969) incorporated herein by reference.

Polyols useful in this invention can be any of a large number of polyols reactive with the isocyanates to form polyurethanes as known in the art. Examples of suitable polyols include but are not limited to, polyester polyols, polyether polyols, modified polyether polyols, polyester ether polyols, castor oil polyols and polyacrylate polyols. Specific polyols further include castor oil and castor oil derivatives (triglyceride of 12-hydroxyoleic acid), poly (ethylene adipates), poly (diethyleneglycol adipates), polycaprolactone diols and polycaprolactone-polyadipate copolymer diols, poly (ethyleneterephthalate) polyols, polycarbonate diols, N,N,N', N'- tetrakis (a hydroxypropyl) ethylenediamine, polytetramethylene ether glycol, ethyleneoxide adducts of polyisypropylene diols, ethylene oxide adducts of polyisypropylene triols. Trademark products include Desmophen, 651A-65, 1300 75 and 800 available from Mobay Corporation of Pittsburg, Pa., Niax E-59 and other available from Union Carbide of Danbury, Conn., Desmophen-550 DU, -1600U, -1920D, and -1150 available from Mobay, and DB oil, Polycin- 12, polycin 55 and Polycin 99F available from CasChem, Inc. of Bayonne, N.J., as well as Desmophen A450, A365 and A160 available from Mobay are useful. Many other polyols are available and can be used as known to those skilled in the arts.

The solvents used are preferably those that do not react with the isocyanate, the polyol or the poly(ethylene oxide) but are solvents for all. The solvents preferably are free of reactive amine, hydroxyl and carboxyl groups. The solvent should further preferably be capable of dissolving the isocyanate, polyol, and poly(ethylene oxide). Suitable solvents include but are not limited to methylene chloride, chloroform, dichloroethane, acetonitrile, dichloethylene and methylene bromide.

Surfactants or wetting agents are used to promote wetting to the substrate as well as adhesion to the substrate by the reaction mixture. Useful wetting agents include the following: perfluoroalkyl ethoxylate mixtures, 2,4,7,9 -tetramethyl 1-5 decyn 4,7- diol and ethylene oxide adducts thereof, #2, 3,5 - dimethyl-1,-hexyn 3 ol, condensation products of ethylene oxide and di (isohexyl-isoheptyl) phenol, condensation products of stearylamine and ethylene oxide, nonyl phenoxypoly (ethyleneoxy) ethanol, and polyethoxylated octylphenol.

Viscosity and flow control agents are used to adjust the viscosity and thixotropy to a desired level. Preferably the viscosity is such that the coating can be formed on the substrate at the desired thickness. Viscosities of from 50 cps to 500 cps can be used although higher or lower viscosities may be useful in certain instances. Viscosity control agents include but are not limited to fumed silica, cellulose acetate butyrate and ethyl acrylate/ 2-ethyl hexyl acrylate copolymer. Flow control agents are preferably used in amounts from 0.05 to 5 percent by weight of coating.

Antioxidants are used to improve oxidative stability of the cured coatings and include but are not limited to tris (3,5-di-t-butyl-4-hydroxy benzyl) isocyanurate, 2,2'-methylenebis (4 methyl-6-t-butyl phenol), 1,3,5 Tri-methyl-2,4,6-tris (3,5-di-t-butyl-4-hydroxybenzyl) benzene, butyl hydroxy toluene, octadecyl 3,5, di-t-butyl 4-hydroxyhydrocinnamate, 4,4'methylenebis (2,6-di-t-butylphenol), p,p'-dioctyl diphenylamine, 1,1,3-tris-(2-methyl-4-hydroxy-5-t-butylphenyl) butane. Antioxidants are preferably used in amounts from 0.01 to 1 percent by weight of coating.

Conventional pigments can be added to impart color or radiopacity, or to increase the desirable appearance of the coatings.

Air release agents or defoamers include but are not limited to polydimethyl siloxanes, 2,4,7,9-tetramethyl-5-decyn-4 7-diol, 2-ethylhexyl alcohol, n-beta-aminoethyl-gamma-amino-propyl-trimethoxysilane. Air release agents are often used in amounts from 0.005 to 0.5 percent by weight of coating.

Depending upon the particular isocyantes and polyols selected, a catalyst may or may not be used. In all cases polyurethanes result. Tertiary amine catalysts can be used in this invention and include N,N-dimethylaminoethanol, N,N-dimethyl cyclo hexylamine Bis-(2-dimethyl aminoethyl) ether, N,N,N',N'N''-pentamethyl-diethylene triamine, N-ethylmorpholine, and 1-(2-hydroxypropyl) imidizole.

Examples of metallic catalyst include, but are not limited to stannous octoate, dibutyl tin dilaurate, dibutyl tin mercaptide, calcium carbonate, ferric acetylacetonate, lead octoate, dibutyl tin diricinoleate.

Where catalysts are used, amounts are typically in the range of 0.05% to 0.5% by weight of coating. Normal catalytic amounts as are known in the arts are preferred.

The following non limiting examples are meant to be illustrative embodiments of the present invention.

EXAMPLE 1

A hydrophilic coating formulation of 2.6% (w/w) total solids was prepared by weighing the following components into a disposable beaker:

a) 3.79g of 60% solution of a trimethylol propane - toluene diisocyanate adduct in PMA (available as CB-60; Mobay Corp.)

b) 1.48g of a castor oil based polyol (Polycin 12; Caschem)

c) 160g of a 3.3% methylene chloride solution of poly(ethylene oxide), mean molecular weight 300,000 (Polyox WSR N 750; Union Carbide Corp.)

d) 186g methylene chloride.

The solution was thoroughly mixed and transferred to a 100ml glass graduated cylinder.

A 10" length of catheter introducer tubing composed of polyether block amide (Pebax 6533; Atochem Inc.) was cleaned in a chlorofluorocarbon solvent (Freon TF; DuPont Inc.) for 3 minutes using an ultrasonic cleaner, then dried at room temperature. This tubing was then dipped in the coating solution to a depth of 8" during 50 seconds. Immediately after dipping, a gentle stream of air was passed through the thus dipped tube for 15 seconds to remove solvent from the inside of the tubing. The tube was then allowed to dry 15 minutes at ambient conditions, then baked 1 hour at 200° F. to effect cure of the coating.

The resulting introducer tubing contained an adherent flexible coating which became very slippery when wet. Continued rubbing of the coating under water with moderate finger pressure did not reduce the lubricity or remove the coating.

The coating was also tested by immersing the tube to a depth of 4" in a 0.5% aqueous solution of Congo Red, for 15 seconds, then rinsing off the excess. This allows visualization of the coating, which absorbs the dye. The tube was then scraped using plastic scrapers formed by cutting rectangular pieces of 0.040" thick polyethylene, polypropylene and nylon.

No dyed material could be seen scraping off, attesting to the durability and adhesion of the coating.

Lubricity was measured by drawing the coated tubing through a slotted later gasket, while wet, and measuring the force required for movement using a load transducer. Movement values of 0.05 to 0.08 lbs. were measured. By comparison, a similar size tube composed of poly tetrafluoroethylene (Teflon, available from E. I. duPont deNemours and Co., Wilmington, Del.) exhibited movement values of 0.35 to 0.39.

The tube was soaked 7 days in water, and retained its properties of lubricity and adhesion.

EXAMPLE 2

A coating formulation suitable for coating natural rubber surfaces was prepared by weighing the following components into a disposable beaker:

a) 2.12g of a 60% solution of a trimethylol propane - toluene diisocyanate adduct in PMA (CB-60; Mobay Corp.)

b) 4.48g of a saturated Polyester Polyol (Multron R-18; Mobay Corp.)

c) 100g of 3.3% methylene chloride solution of poly (ethlyene oxide), mean molecular weight 300,000 (Polyox WSR N-750; Union Carbide Corp.)

d. 114g of methylene chloride.

Total solids of this solution was 4.1% (w/w). The solution was thoroughly mixed and transferred to a 100ml glass graduated cylinder.

A 13F urological catheter composed of natural rubber with a chlorinated surface was cleaned as in Example 1.

The catheter was then dipped in the coating solution to a depth of 9" during 60 seconds. Immediately after dipping, coating solution retained inside the catheter tip was removed using a syringe, and a gentle stream of air was purged through the inside for 15 seconds to remove solvent.

The catheter was allowed to dry 15 minutes at ambient conditions, then baked 1 hour at 200° F. to effect cure of the coating.

The resulting product was a rubber catheter containing an adherent, flexible coating. Upon contact with water the coating became very lubricious. Repeated rubbing of the coating under water with moderate finger pressure did not reduce the slipperiness.

The coating was tested using Congo Red as in Example 1 with the same results. Furthermore, the rubber catheter could be stretched 300% without any loss of coating adhesion. This catheter was tested for coefficient of friction according to ASTM D1894-87, by placing it in a 100° F. water bath. Coefficient of friction values of 0.022 were measured initially, and 0.045 after 16 days in water. By comparison, a similar catheter coated with polytetrafluoroethylene (Teflon, available from E. I. duPont deNemours and Co., Wilmington, Del.) exhibited coefficient of friction values of 0.40.

EXAMPLE 3

A hydrophilic coating formulation suitable for latex rubber surfaces was prepared by weighing the following components into a disposable beaker:

a. 1.59g of a 60% solution of a trimethylol propane-toluene diisocyanate adduct in PMA (CB 60: Mobay Corp.)

b. 3.36g of a saturated Polyester polyol (multron R-18; Mobay Corp.)

c. 100g of a 3.3% methylene chloride solution of poly (ethylene oxide). Mean molecular weight 300,000 (polyox WSR N-750: Union Carbide Corp).

Total solids of this solution was 3.5% (w/w). The solution was thoroughly mixed and transferred to a 100ml glass graduated cylinder.

A urological catheter composed of latex with a chlorinated surface was dipped to a depth of 9" in the coating solution during 60 seconds. Immediately after dipping air was passed gently through the inside lumen to remove solvent. The catheter was dried at ambient conditions for 30 minutes, then baked 1 hour at 200° F.

The resulting catheter contained an adherent, highly flexible coating which became lubricious on contact with water. Performance of this coating was the same as described for Example 2. In addition, an integral latex balloon at the end of the catheter was inflated using 20cc water. The coating covering this balloon remained adherent and intact after inflation.

This catheter was tested for coefficient of friction according to ASTM D1894-87, by placing the catheter in a 100° F. water bath. Coefficient of friction values of 0.02 were measured initially, and 0.044 at 16 days in water. This attests to lubricity of this coating. By comparison, a similar catheter coated with polytetrafluoroethylene (Teflon available from E. I. duPont deNemours and Co., Wilmington, Del.) exhibited a coefficient of friction value of 0.40.

EXAMPLE 4

A hydrophilic coating formulation suitable for coating many thermoplastic urethanes was prepared by weighing the following components into a disposable beaker.

a. 5.63g of 60% solution of a trimethylol propane - toluene diisocyanate adduct in PMA CB-60; Mobay Corp.)

b. 4.38g of a Polyester polyol (Multron R-12A: Mobay Corp.)

c. 167g of a 6% acetonitrile solution of poly (ethylene oxide). mean molecular weight 300,000 (polyox WSR N 750; Union Carbide Corp.)

d. 156g of acetonitrile.

Total solids of this solution was 5.3% (W/W). The solution was thoroughly mixed and transferred to a 250 ml glass graduated cylinder.

A 15" length of catheter tubing composed of a thermoplastic polyetherurethane (Estane 58092; B.F. Goodrich Co.) was dipped to a depth of 12" in the coating solution during 75 seconds, and treated as in examples 1-3.

The resulting tubing contained an adherent, flexible coating which became slippery when wet with water, and which remained lybricious after repeated finger rubbing. Scraping with plastic scrapers did not remover the coating. Lubricity was retained after 7 days immersion in water.

Examples 5 and 6 indicate NCO/OH ratios of 0.8 and 2.0 respectively. The coatings of these examples are not as durable as where the NCO/OH ratios are at 1.1 as in Examples 1-4. These examples illustrate the advantages of desirable selection of NCO to OH ratio with particular materials used.

EXAMPLE 5

A hydrophilic coating formulation of 2.6% (w/w/) total solids was prepared by weighing the following components into a disposable beaker:

a) 3.79g of 60% solution of a trimethylol propane - toluene diisocyanate adduct in PMA (available as CB 60; Mobay Corp.)

b) 2.04g of a castor oil based polyol (Polycin 12; Caschem)

c) 160g of a 3.3% methylene chloride solution of poly(ethylene oxide), mean molecular weight 300,000 (Polyox WSR-N 750; Union Carbide Corp.)

d) 186g methylene chloride.

The solution was thoroughly mixed and transferred to a 100ml glass graduated cylinder.

A 10" length of catheter introducer tubing composed of polyether block amide (Pebax 6533; Atochem Inc.) was cleaned in a chlorofluorocarbon solvent (Freon TF; DuPont Inc.) for 3 minutes using an ultrasonic cleaner, then dried at room temperature. This tubing was then dipped in the coating solution to a depth of 8" during 50 seconds. Immediately after dipping, a gentle stream of air was passed through the thus dipped tube for 15 seconds to remove solvent from the inside of the tubing. The tube was then allowed to dry 15 minutes at ambient conditions, then baked 1 hour at 200° F. to effect cure of the coating.

The resulting introducer tubing contained an adherent flexible coating which became very slippery when wet. Continued rubbing of the coating under water with moderate finger pressure did not reduce the lubricity or remove the coating.

EXAMPLE 6

A hydrophilic coating formulation of 2.6% (w/w) total solids was prepared by weighing the following components into a disposable beaker:

a) 4.31g of 60% solution of a trimethylol propane toluene diisocyanate adduct in PMA (available as CB-60; Mobay Corp.)

b) 0.93g of a caster oil based polyol (Polycin 12: Caschem)

c) 160g of a 3.3% methylene chloride solution of poly(ethylene oxide), mean molecular weight 300,000 (Polyox WSR-N 750; Union Carbide Corp.)

d) 186g methylene chloride.

The solution was thoroughly mixed and transferred to a 100ml glass graduated cylinder.

A 10" length of catheter tubing composed of polyether block amide (Pebax 6533; Atochem Inc.) was cleaned in a chloroflurocarbon solvent (Freon TF; DuPont Inc.) for 3 minutes using an ultrasonic cleaner, then dried at room temperature. This tubing was then dipped in the coating solution to a depth of 8" during 50 seconds. Immediately after dipping, a gentle stream of air was passed through the thus dipped tube for 15 seconds to remove solvent from the inside of the tubing. The tube was then allowed to dry 15 minutes at ambient conditions, then baked 1 hour at 200° F. to effect cure of the coating.

The resulting introducer tubing contained an adherent flexible coating which became very slippery when wet. Continued rubbing of the coating under water with moderate finger pressure did not reduce the lubricity or remove the coating.

While specific embodiments of the present invention have been shown and described, many variations thereof are possible as will be apparent to those skilled in the arts. In all cases, it is important to form a coating from a one mixture liquid containing coating material. This aids in closely controlling the coating as to the ratio of (polyisocyanate and polyol) to poly(ethylene oxide) without relying on whatever quantities happen to deposit from the respective wet films produced on multiple, independent dipping. It is preferred to use a true polyurethane complex so as to produce the required physical characteristics for the coating, including the adherence to the underlying substrate. Because polyols are used, selections can be made to tailor the adhesion, abrasion resistance and flexibility of the coatings as may desired for particular applications in the body. By varying the coating solids level, coating thicknesses can vary from less than 10 microns to 125 microns, or even greater, as may be desired. In all cases, the coating is hydrophilic in the sense that it will take up at least 10% of its weight of water.

What is claimed is:

1. An abrasion resistant, hydrophilic lubricious, organic coating comprising a cross-linked polyurethane and a polyethylene oxide formed from the reaction on a (surface) substrate to be coated, of a mixture containing, an isocyanate, a polyol and a polyethylene oxide in a carrier liquid to form a (polyurethane) coating having good adherence to the substrate and good anti-friction properties.

2. An abrasion resistant coating in accordance with claim 1, wherein the ratio by weight of isocyanate and polyol to poly(ethylene oxide) is in the range of from 0.25 to 6.0.

3. An abrasion resistant coating in accordance with claim 2 wherein said ratio is in the range of from 0.75 to 2.0.

4. An abrasion resistant coating in accordance with claim 1 wherein the stoichimetric ratio of total NCO groups to total OH groups in said mixture varies from 0.6 to 3.5.

5. An abrasion resistant coating in accordance with claim 4 wherein said poly(ethylene oxide) has a mean molecular weight in the range of from about 50,000 to about 5,000,000.

* * * * *